US009468473B2

(12) United States Patent
Blain

(10) Patent No.: US 9,468,473 B2
(45) Date of Patent: Oct. 18, 2016

(54) APPARATUS FOR PROMOTING MOVEMENT OF NUTRIENTS TO INTERVERTEBRAL SPACE AND METHOD OF USE

(71) Applicant: Spinal Elements, Inc., Carlsbad, CA (US)

(72) Inventor: Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 14/746,408

(22) Filed: Jun. 22, 2015

(65) Prior Publication Data

US 2015/0359569 A1 Dec. 17, 2015

Related U.S. Application Data

(63) Continuation of application No. 13/534,307, filed on Jun. 27, 2012, now Pat. No. 9,089,438.

(60) Provisional application No. 61/502,201, filed on Jun. 28, 2011.

(51) Int. Cl.

| | |
|---|---|
| ***A61F 2/44*** | (2006.01) |
| ***A61B 17/70*** | (2006.01) |
| ***A61F 2/46*** | (2006.01) |
| *A61F 2/30* | (2006.01) |

(52) U.S. Cl.

CPC ........... *A61B 17/7061* (2013.01); *A61F 2/442* (2013.01); *A61F 2/4455* (2013.01); *A61F 2/46* (2013.01); *A61F 2002/30092* (2013.01); *A61F 2002/30224* (2013.01); *A61F 2002/30235* (2013.01); *A61F 2002/30237* (2013.01); *A61F 2002/30616* (2013.01); *A61F 2002/448* (2013.01); *A61F 2002/4475* (2013.01); *A61F 2310/00011* (2013.01); *A61F 2310/00023* (2013.01); *A61F 2310/00293* (2013.01); *A61F 2310/00359* (2013.01); *A61F 2310/00976* (2013.01)

(58) Field of Classification Search

CPC ........... A61F 2002/30622; A61F 2002/30677; A61F 2002/448; A61F 2210/0061

USPC ..................... 606/246–249; 623/17.11–17.16

See application file for complete search history.

(56) References Cited

U.S. PATENT DOCUMENTS 5,336,223 A 8/1994 Rogers
6,056,749 A * 5/2000 Kuslich ................ A61B 17/025 606/247
6,086,589 A 7/2000 Kuslich et al.
6,328,765 B1 12/2001 Hardwick et al.
6,533,817 B1 3/2003 Norton et al.
6,607,530 B1 8/2003 Carl et al.

(Continued)

*Primary Examiner* — Mary Hoffman
*Assistant Examiner* — Tara R Carter
(74) *Attorney, Agent, or Firm* — Knobbe, Martens, Olson & Bear, LLP

(57) ABSTRACT

Devices and methods are disclosed for treating an intervertebral space. A device is provided that extends from the middle of at least one vertebral body to the disc space between two adjacent vertebrae. The device allows nutrients, such as bone marrow, blood, etc., to migrate from the vertebral body to the disc space to help promote fusion of the two adjacent vertebral bodies. The device can be tubular, perforated and can be made of an absorbent or wicking material that is able to promote the nutrients to travel through the apparatus.

18 Claims, 7 Drawing Sheets

(56) References Cited

U.S. PATENT DOCUMENTS 6,887,272 B2 5/2005 Shinomiya et al.
7,531,004 B2 5/2009 Bagga et al.
7,534,451 B2 5/2009 Erbe et al.
7,547,317 B2 * 6/2009 Cragg ................ A61B 17/1671 128/898
8,740,979 B2 6/2014 Matsuura et al.
9,089,438 B2 7/2015 Blain
2001/0023349 A1 9/2001 VanTassel et al.
2002/0173796 A1 11/2002 Cragg
2003/0158557 A1 8/2003 Cragg et al.
2004/0210209 A1 10/2004 Yeung et al.
2004/0215343 A1 10/2004 Hochschuler et al.
2004/0230195 A1 11/2004 Kaikkonen et al.
2004/0230305 A1 11/2004 Gorensek et al.
2005/0113929 A1 * 5/2005 Cragg .................... A61B 17/70 623/17.16
2005/0177237 A1 8/2005 Shappley et al.
2005/0246023 A1 11/2005 Yeung
2006/0122704 A1 6/2006 Vresilovic et al.
2006/0206209 A1 9/2006 Cragg et al.
2006/0247600 A1 * 11/2006 Yeung .................... A61B 17/00 604/500
2007/0067025 A1 3/2007 Schwartz
2007/0106383 A1 5/2007 Abdou
2007/0213827 A1 9/2007 Arramon
2008/0215152 A1 9/2008 Matsuura et al.
2011/0054615 A1 3/2011 Buckland et al.

* cited by examiner

APPARATUS FOR PROMOTING MOVEMENT OF NUTRIENTS TO INTERVERTEBRAL SPACE AND METHOD OF USE

CROSS-REFERENCE TO RELATED APPLICATIONS

This application is a continuation of U.S. patent application Ser. No. 13/534,307, filed Jun. 27, 2012, which claims priority under 35 U.S.C. §119(e) to U.S. Provisional Patent Application No. 61/502,201, filed Jun. 28, 2011, the disclosure of each is incorporated by reference herein in its entirety.

FIELD OF THE INVENTION

This application relates generally to spinal fixation, an apparatus, and a method for implanting an apparatus for promoting movement of nutrients from a vertebral body into the disc space between vertebral bodies to promote fusion between vertebral bodies.

DESCRIPTION OF THE RELATED ART

Advancing age, as well as injury, can lead to degenerative changes in the bones, discs, joints and ligaments of the spine, producing pain and instability. In some extreme cases, alleviation of the problems can be accomplished by spinal fusion. Spinal fusion is where two or more vertebrae of the spinal column are fused together to eliminate the motion between the fused vertebrae. Spinal fusion is used to treat conditions where the spine exhibits instability. Spine instability may result from causes such as fracture, scoliosis and spondylolisthesis, where one or more vertebrae move in a forward direction relative to the other vertebrae. Spinal fusion with discectomy is also performed for herniations of the discs. This surgery involves removal of a portion or all of the affected disc and fusion of the adjacent vertebrae. Traditionally, bone grafts or vertebral implants have been used to fuse the vertebrae. Notwithstanding the foregoing, there remains a need for improved methods and devices for treating spinal instability.

SUMMARY OF THE INVENTION

Devices and methods are disclosed for treating the intervertebral space. A device is provided that extends from the middle of at least one vertebral body to the disc space between two adjacent vertebrae. The device can allow nutrients, such as bone marrow, blood, etc., to migrate from the vertebral body to the disc space to help promote fusion of the two adjacent vertebral bodies. In some embodiments, the device can be tubular and perforated. In some embodiments, the device can be made of an absorbent or wicking material that is able to promote the nutrients to travel through the apparatus.

In some embodiments, the device comprises a porous member having a first end and a second end wherein the first end is in communication with the second end to promote transfer of nutrients from the first end to the second end. The porous member may be an elongate tube. In some embodiments, the porous material may be flexible.

The method includes creating a hole in the endplate of at least one vertebral body to access the middle portion of the vertebrae with the device. The formation of the hole can be accomplished freehanded using a rasping or cutting tool. In some embodiments, the cutting instrument can be configured to secure into the intervertebral space or attach to the vertebral body for a more stable and accurate hole formation. In other embodiments, the perforation can be performed by an implant that is placed in the intervertebral space.

In some embodiments, the method may include accessing an endplate of a vertebral body, perforating the endplate of a vertebral body, providing an implant for treating the spine comprising a porous member configured to promote transfer of nutrients, inserting the implant into a spinal column so that a first end of the implant is adjacent a cancellous bone portion of a vertebra and a second end of the implant is adjacent an intervertebral space. The method may include using a drill to create a hole in the endplate. In some embodiments, the drill may be curved. In some embodiments, the endplate perforated is inferior to the intervertebral disc space and faces a downward direction.

The method may further comprise placing an interbody spacer within a disc space between the endplate and an opposing end plate. In some embodiments, a portion of the device may be placed within the interbody spacer. The interbody spacer may be placed within the disc space before the device is inserted, or the device may be placed within the disc space before the interbody spacer is implanted. In some embodiments, the device and interbody spacer may be inserted simultaneously.

Some methods may include removing a portion of the annulus to create access to a disc space, preparing the disc space for fusion, creating a hole in the endplate, placing a device comprising a wicking material or perforated tube in the hole, and placing an interbody device within the disc space. The interbody device may be placed into the disc space before the device is placed in the hole. In other embodiments, the interbody device may be placed into the disc space after the device is placed in the hole. The device may extend into at least a portion of the interbody device. The hole in the endplate may be formed after the interbody device is placed within the disc space. In other embodiments, the hole may be formed before the interbody device is placed within the disc space. The hole may be created using a drilling jig. The above embodiments and methods of use are explained in more detail below.

DETAILED DESCRIPTION OF THE PREFERRED EMBODIMENT

Advancing age, as well as injury, can lead to degeneration in the bones, discs, joints, and ligaments of the spine producing pain from nerve root compression or impingement of the spinal cord. Under certain circumstances, alleviation of pain can be provided by performing a spinal fusion. Spinal fusion is a procedure that involves joining two or more adjacent vertebrae so that they no longer are able to move relative to each other. Spinal fusion typically involves placing bone graft between vertebrae in the area usually occupied by the intervetebral disc. In many procedures, a portion of the disc is removed and a device (e.g., an interbody spacer) can be placed between the vertebrae to maintain spine alignment and disc height. For example, in some embodiments the disc nucleus or portions thereof is removed while leaving the disc annulus. Bone graft can be placed between the vertebrae before, while or after positioning the interbody spacer. Fusion can then occur between the endplates of the vertebrae. In most cases, the fusion is augmented with fixation between the vertebral bodies. Such fixation between vertebral bodies can be accomplished using various fixation devices, such as, for example, pedicle screws and rod constructions, transfacet and transpedicle screws, interbody spacers, rods, plates and cages, which can be used to stabilize a pair of vertebral bodies together.

Figure 1:
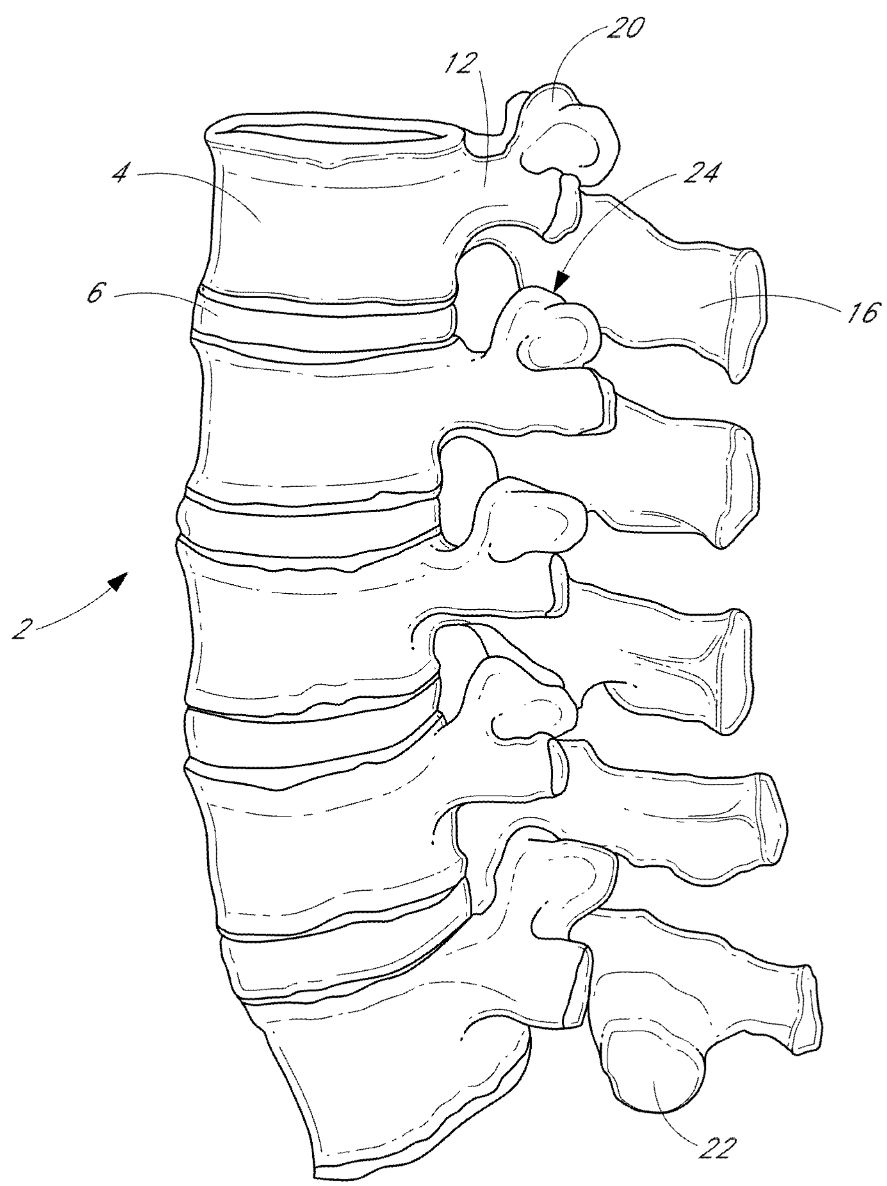
FIG. 1 is a lateral elevational view of a portion of the vertebral column.
Figure 2A:
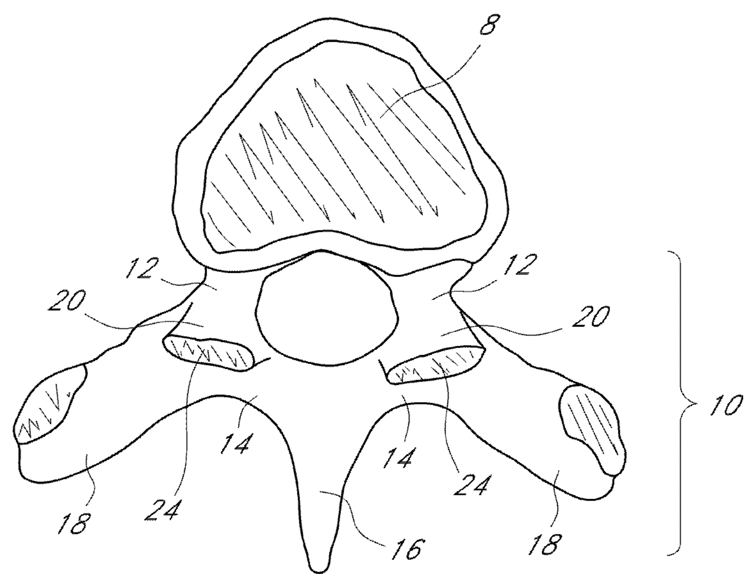
FIGS. 2A and 2B are superior and lateral elevational views of a thoracic vertebra.
Figure 2B:
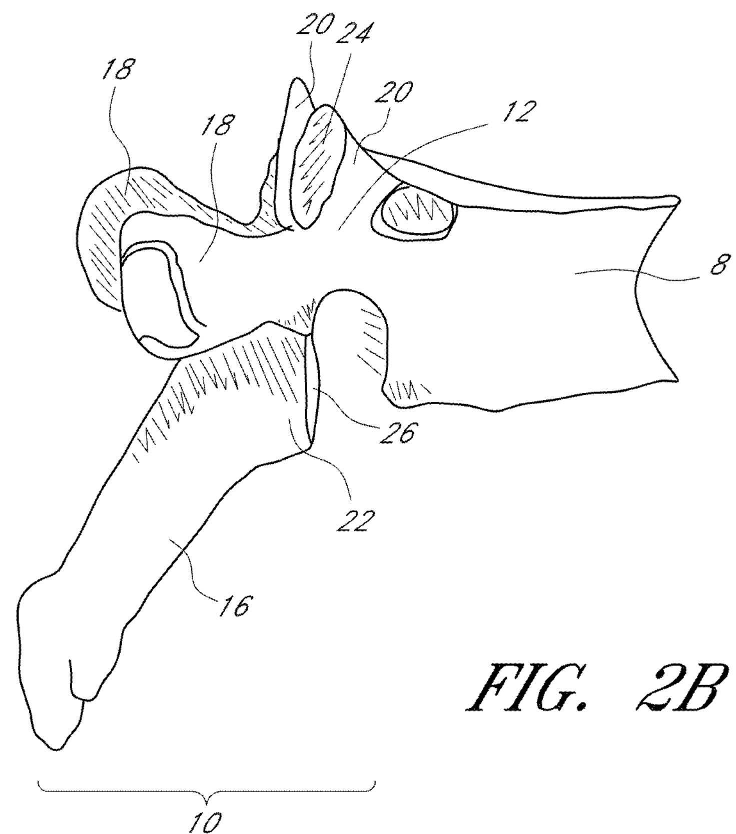

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-L5), five fused sacral (S1-S5) and four fused coccygeal vertebrae. FIGS. 2A and 2B depict typical thoracic vertebrae. Each vertebra includes an anterior body 8 with a posterior arch 10. The posterior arch 10 comprises two pedicles 12 and two laminae 14 that join posteriorly to form a spinous process 16. Projecting from each side of the posterior arch 10 are a transverse 18, superior 20 and inferior articular process 22. The facets 24, 26 of the superior 20 and inferior articular processes 22 form facet joints 28 with the corresponding articular processes of the adjacent vertebrae.

Figure 3:
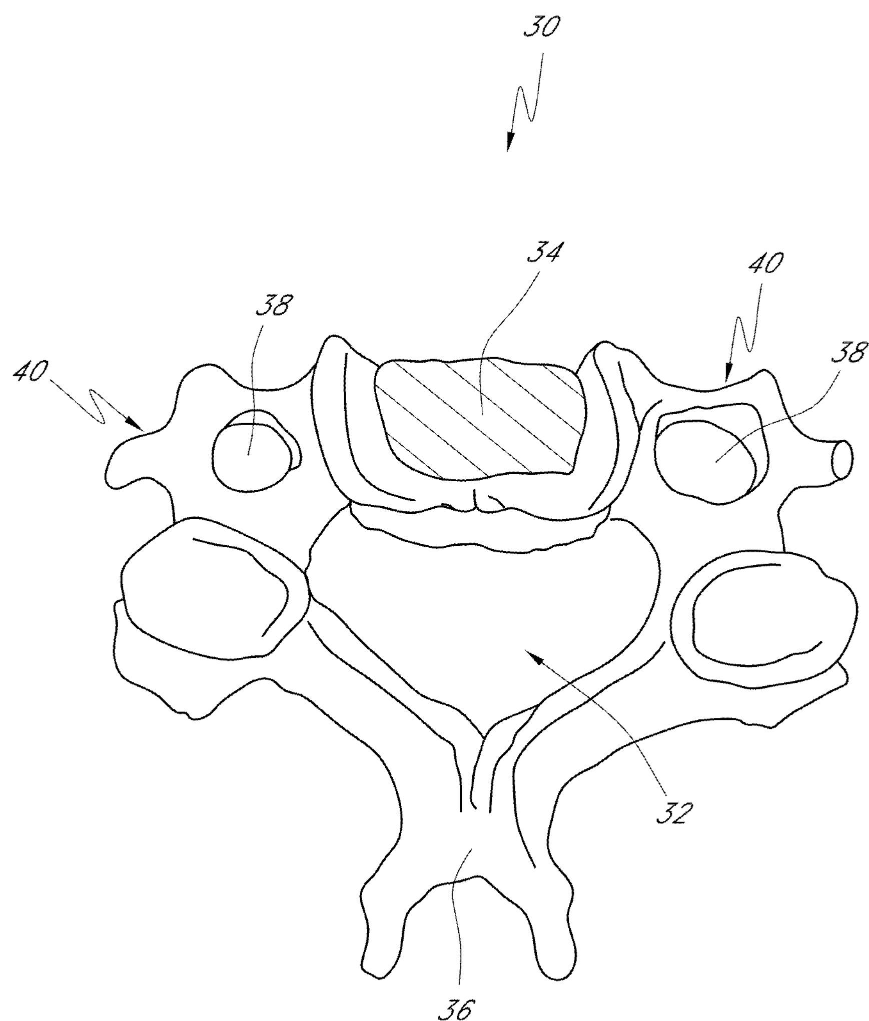
FIG. 3 illustrates a superior elevational view of a cervical vertebra.

The typical cervical vertebrae 30, shown in FIG. 3, differ from the other vertebrae with relatively larger spinal canals 32, oval shaped vertebral bodies 34, bifid spinous processes 36 and foramina 38 in their transverse processes 40. These foramina transversaria 38 contain the vertebral artery and vein. The first and second cervical vertebrae also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

Figure 4:
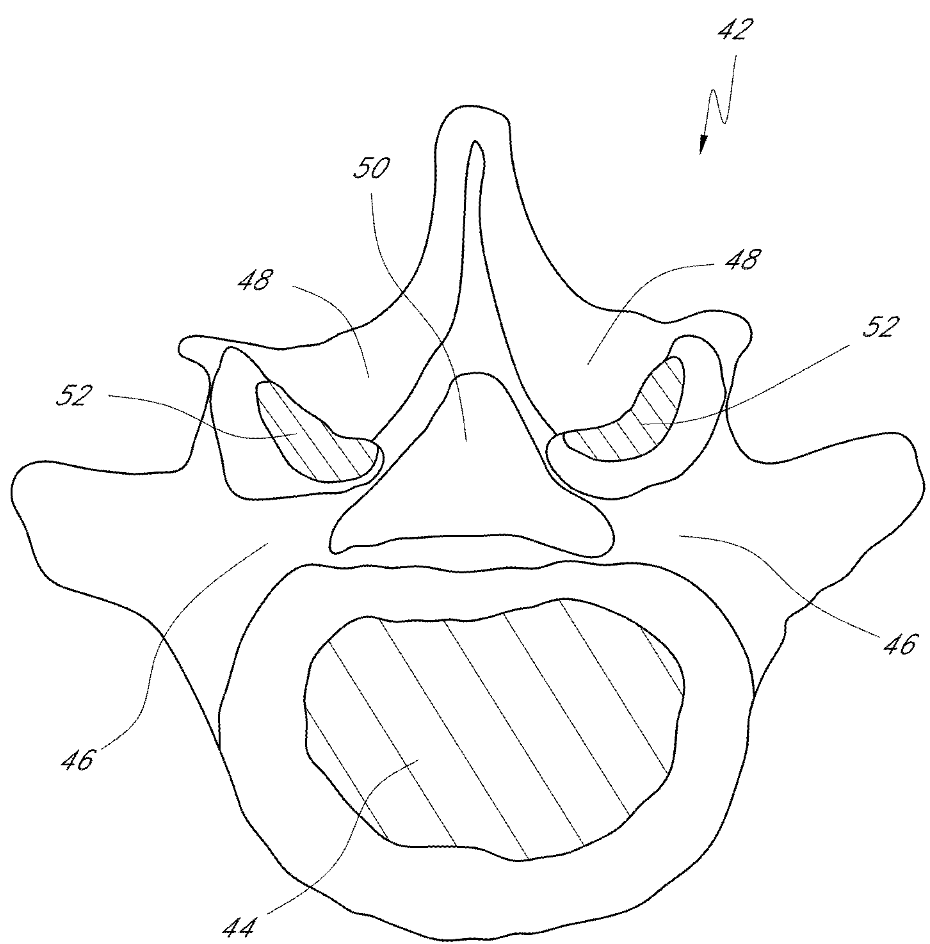
FIG. 4 represents a superior elevational view of a lumbar vertebra.

Referring to FIG. 4, the typical lumbar vertebrae 42 is distinguishable from the other vertebrae by the absence of foramina transversaria and the absence of facets on the surface of the vertebral body 44. The lumbar vertebral bodies 44 are larger than the thoracic vertebral bodies and have thicker pedicles 46 and laminae 48 projecting posteriorly. The vertebral foramen 50 is triangular in shape and larger than the foramina in the thoracic spine but smaller than the foramina in the cervical spine. The superior 52 and inferior articular processes (not shown) project superiorly and inferiorly from the pedicles, respectively.

An aspect of at least one of the embodiments disclosed herein includes the realization that a device can be provided that can allow nutrients, such as bone marrow, blood, etc., to migrate from the cancellous bone portion 70 of the vertebral body 4 to the intervertebral space 60 to help promote fusion of the two adjacent vertebral bodies.

Figure 5:
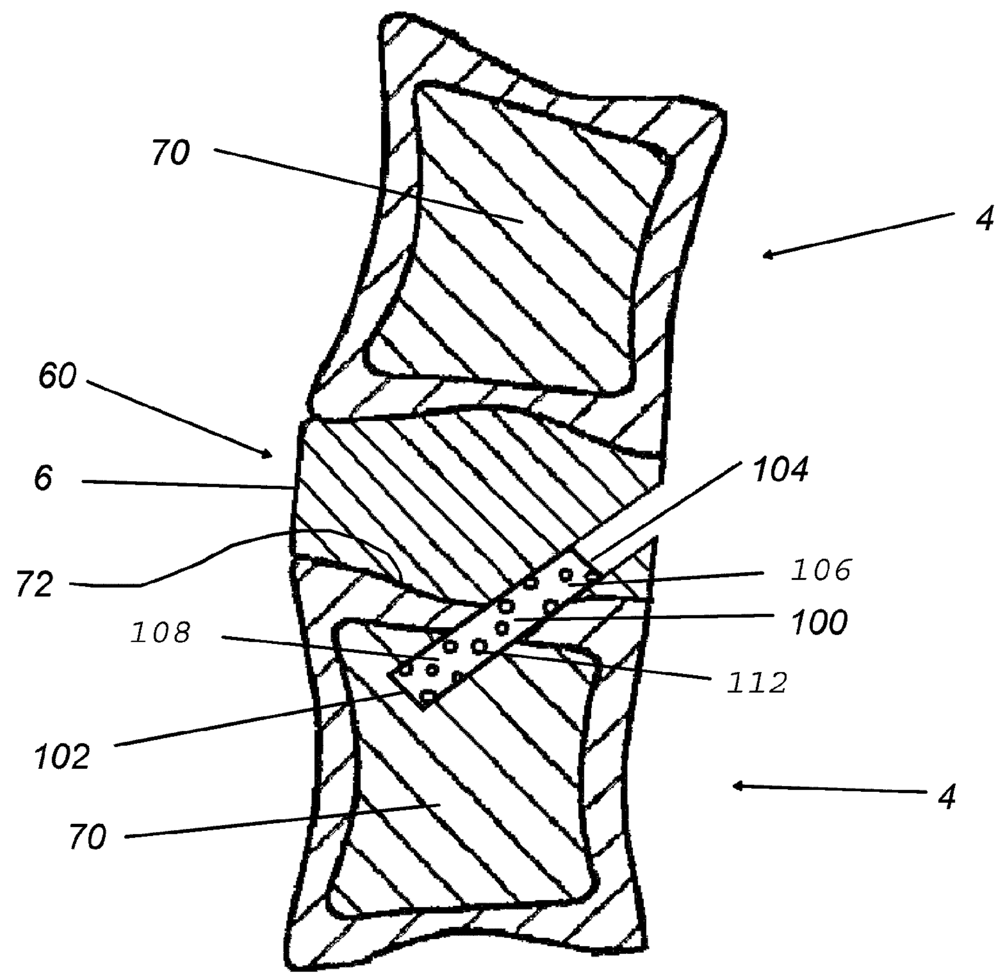
FIG. 5 is an elevational view of adjacent vertebrae and an apparatus according to an arrangement.

As illustrated in FIG. 5, the device 100 can be an elongate member that extends from the cancellous bone portion 70 at a first end 102 of the apparatus to the intervertebral space 60 at the second end 104 of the device 100. The device 100 can be a tube or a perforated member. In the illustrated embodiment, the device 100 has a plurality of holes 112 that extend at least partially through the device 100 that can provide a frame for growth and/or transfer of nutrients through the device 100. In some embodiments, the device 100 can have indentations, holes or pores for allowing bony ingrowth or filling with bony matrix or graft materials, as described further below. In some embodiments, a first section 108 near the first end 102 of the apparatus may have different holes, pores, or indentations than a second section 106 near the second end 104 of the apparatus such that the surface of the first section 108 may be optimized for wicking nutrients into the interior of the apparatus, and the second section 106 may be optimized for delivery of the nutrients to the surrounding area of the intervertebral space and/or tissue ingrowth into the second section 106 of the device 100.

The device 100 may be generally circular in cross section, or may be triangular, elliptical, oval, rectangular or any other cross-sectional shape. The device 100 may have a first cross sectional shape and/or size toward the first end 102 of the device, and transition to a different cross sectional shape or larger size toward the second end 104 of the device. This may help ensure that the second end 104 of the device maintains its position in the intervertebral space 60, rather than subsiding into the cancellous bone portion 70. It may also be advantageous in increasing the surface area for distribution of the nutrients, marrow, or cells.

The device 100 can include, be made of, treated, coated, filled, used in combination with, or contain artificial or naturally occurring materials suitable for implantation in the human spine. These materials include any source of osteogenesis, bone growth-promoting materials, bone derived substances, bone morphogenetic proteins, hydroxyapatite, genes coding for the production of bone, and bone including, but not limited to, cortical bone. Preferably, the device 100 is made of an absorbent material or wicking material that is able to promote the travel of nutrients through the device 100. The device can also be formed of material such as metal including, but not limited to, titanium and its alloys, surgical grade plastics, plastic composites, ceramics, or other materials suitable for use as a spinal fusion implant. The device 100 may comprise one or more materials as a covering and comprise a different material in the center of the device. In some embodiments, the device 100 may be hollow in part or throughout. In some embodiments, the device may comprise channels along its surface or internally, which may contain bone graft, factors promoting bone growth, or any of a variety of desirable materials, such as antibiotic agents.

In some embodiments, the device 100 comprises a radiolucent material, a radio-opaque material, or a combination thereof. A device 100 that is partially or completely radiolucent may be advantageous when evaluating the effect of the implant post-implantation. A device 100 that has a small quantity of radio-opaque material strategically placed, for example, a longitudinal strip, may easily have its position confirmed intra- or post-operatively.

The device 100 can include, at least in part, materials that are bioabsorbable in the body. In some embodiments, the device 100 can comprise a polyaryl polymer, including but not limited to PEK, PEEK, PEKK, PEKEKK or a blend thereof. Other combinations can also be used as is known by those with skill in the art.

The device 100 can be formed of a porous material or can be formed of a material that intrinsically participates in the growth of bone from one of adjacent vertebral bodies to the other of adjacent vertebral bodies. The device 100 can be treated with, coated with, or used in combination with substances to inhibit scar tissue formation. The device 100 can be modified, or used in combination with materials to provide antibacterial properties, such as, but not limited to, electroplating or plasma spraying with silver ions or other substance. The device 100 can optionally comprise an electrical source to provide iontophoresis of the silver ions into the surrounding tissue to prevent infection. The anti-bacterial properties may include bactericidal and/or bacteriostatic characteristics. Similarly, anti-fungal characteristics may also be provided. Any of these materials as appropriate may be used at any time after the implant is inserted.

In some embodiments, the device 100 can be flexible and can conform to the shape of the hole formed in the vertebra 4. For example, the device 100 can be flexible to be implanted into a curved hole, as explained further below. In other embodiments, the device can be rigidly curved with the same curved shape as the curved hole.

In some embodiments, the device 100 may comprise a flexible material supported by one or more struts; for example, running longitudinally between the first end 102 and the second end 104 either on the perimeter of the device 100 or along its central longitudinal axis. The struts may be comprised of any suitable material, including shape memory alloys such as Nitinol, other metals, polypropylene, or other plastics. The one or more struts may be arranged to form a frame or in such a manner that they form a web. Having the struts supporting a more flexible material of which the implant is comprised may allow implantation in a reduced configuration, with expansion to the native configuration after implantation. There may be, for example, a helical supporting strut which may be compressed such that the longitudinal length of the elongate implant 100 is reduced upon implantation. This may be advantageous, for example, in allowing the implant 100 to fit within, for example, an interbody spacer during insertion of the spacer between the inferior and superior surfaces. Upon insertion, when the implant passes over the hole in the endplate 72 of a vertebral body prepared for it, the strut may resume its native shape and the first end of the implant enter the cancellous bone of the vertebra for wicking nutrients into the intervertebral space.

In some embodiments, the device may further comprise an anchoring devices for maintaining its position in the cancellous bone portion 70 of the vertebra 4. For example, one or more radially placed members may bias toward the second end 104 of the device 100 during insertion, but once inserted past the vertebral end plate, 72, may angle outward, and resist backing out of the device. One or more longitudinal struts may allow compaction of the device during insertion, but may expand outward to create a widened cross section within the cancellous bone 70 which resists backing out of the device.

The device 100 may be provided in multiple sizes, materials, or configurations. For example, the device may have a length in the range of 1-5 cm, or 2-4 cm. The device may have a diameter of about 3 mm, 4 mm, 5 mm, 6 mm, 7 mm, 8 mm, 9 mm, 1 cm, 1.1 cm, 1.2 cm, 1.3 cm, 1.4 cm, 1.5 cm, 1.6 cm, 1.7 cm, 1.8 cm, 1.9 cm, or 2 cm. The device may have pores or holes on its surface which may range in size from 1 μm to 4 mm. In some instances, the size of the holes may be 3 μm to 2 mm. Pore size may be consistent throughout, or may vary along the length of the device. The device may have a constant diameter along its length or it may have flared ends on either or both the first end 102 and the second end 104 for more efficient uptake and/or delivery of nutrients.

In some embodiments, a single first section 108 may divide into two or more sections toward the second end 104, such that nutrients wicked up from the cancellous bone 70 may be distributed more effectively throughout the intervertebral space. In some embodiments, the inserter may be configured to manipulate these second sections into position. In some embodiments, the implant is compressed during insertion and resumes an expanded native configuration upon implantation.

Figure 6:
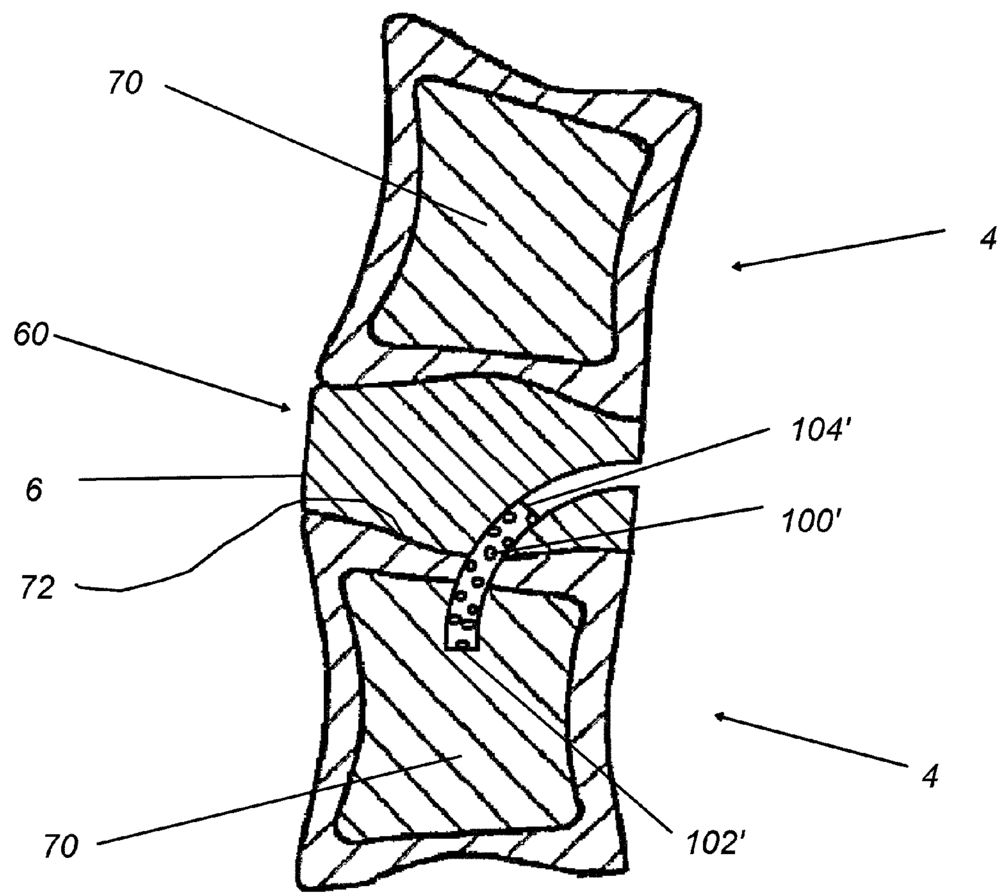
FIG. 6 is an elevational view adjacent vertebrae and an apparatus according to another arrangement.

The method of implanting the device 100 can include creating a hole in the endplate 72 of at least one of an adjacent vertebral body 4 to access the cancellous bone portion 70 of the vertebrae 4. The path to the endplate can be created from the side of the intervertebral space 60 and into the endplate 72, as illustrated in FIG. 6. Depending on the surgical approach selected, the intervertebral space 60 and endplate 72 of the vertebral body 4 may be entered from the posterior, postero-lateral, lateral, or anterior surfaces. In some embodiments, a drill can be used to form a hole through the fibrous disc 6 and into the endplate 72 of the vertebrae 4. The hole can extend through the endplate 72 and into the cancellous bone portion 70. After the hole is formed, the device 100 can be inserted into the hole so that a first portion 104 of it is in the cancellous bone portion 70 and a second portion 106 is in the intervertebral disc space 60.

In some embodiments, the endplate 72 can be perforated freehanded using a rasping or cutting tool. In other embodiments, the cutting instrument can be configured to secure into the intervertebral space 60 or attach to the vertebral body 4 for a more stable and accurate perforation. In other embodiments, the perforation can be performed by an implant that is placed in the intervertebral space 60. If a guide is used for the perforating tool, the guide may also be used for insertion of the implant 100.

With reference to FIG. 6, in some embodiments the path between the cancellous bone portion 70 and the intervertebral space 60 can be curved, as shown in FIG. 2. A curved drill or awl may be used to create the curved path. A curved path can advantageously provide a pathway between the cancellous bone portion 70 and the intervertebral space 60 in situations where a straight pathway is difficult or impossible to form. In other embodiments, a right angle drill or awl or other perforating tool may be used to create a hole in the vertebral end plate 72 generally perpendicular to the end plate. Insertion of a flexible device 100 may be accomplished through a right angle guide or with other appropriate instrumentation. Insertion of a hollow device may be accomplished over a passer.

In some embodiments, graft material such as autograft, allograft, xenograft or synthetic material can be inserted into the disc space before or after the device 100 is implanted. Synthetic graft material may be ceramic-based, silicon-based or calcium-based. The graft material may also include osteoinductive factors to promote bone ingrowth. One skilled in the art will appreciate that there are many varieties of synthetic and non-synthetic graft materials and constituents that may be used to fill the disc space to promote fusion.

As described above, in many procedures, a substantial portion of the disc is removed (e.g., portions of the nucleus can be removed leaving the annulus) and a device (e.g., an interbody spacer) (not shown) can be placed between the vertebrae to maintain spine alignment and disc height. Bone graft can be placed between the vertebrae before, while or after positioning the interbody spacer. Fusion can then occur between the endplates of the vertebrae. The device 100 described above can promote fusion by providing a path for nutrients to flow from the vertebral body into the disc space. In most cases, the fusion is augmented with fixation between the vertebral bodies. Such fixation between vertebral bodies can be accomplished using various fixation devices, such as, for example, pedicle screws and rod constructions, trans-facet and transpedicle screws, interbody spacers, rods, plates and cages, which can be used to stabilize a pair of vertebral bodies together. The device may be particularly advantageous when fixation devices such as plates are used, as preparation of the disc space and insertion of the device may be accomplished with significantly less trauma than many conventional means of promoting fusion.

In the figures discussed above, the device 100 is depicted as being placed in the lower vertebra. In addition, or in the alternate, a device 100 can be placed in the upper vertebra. In such embodiments, gravity could help transfer nutrients from the device into the disc space. In such embodiments, to prevent the first portion 108 from being dislodged from the vertebral body by gravity, an anchoring means may be provided with the device, or it may be configured such that it is compressible radially during insertion, but expands after placement.

Figure 7:
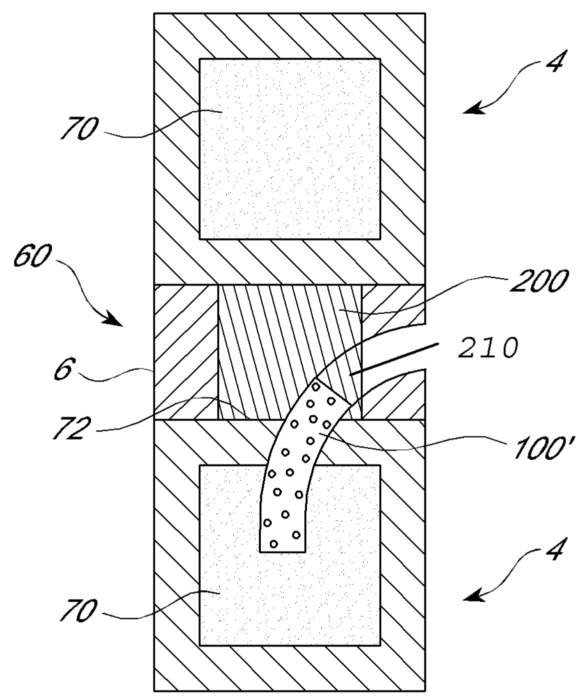
FIG. 7 is an elevational view adjacent vertebrae and an apparatus according to another arrangement.

As discussed above, in some embodiments, the device 100 can lie within an intervertebral body spacer positioned within the disc space. FIG. 7 illustrates one example of such arrangement in which the device 100' can lie within an interbody spacer 200 positioned within the disc space 60. In other embodiments, the device can be straight. In other arrangements, the interbody spacer 200 can be positioned near and/or adjacent the device 100 in the disc space. In certain embodiments, the intervertebral body spacer can be configured to contain the nutrients in the disc space and prevent them from migrating out. The order of placing the interbody device 200 and wicking device 100 into the spice can vary. For example, in one embodiment, a portion of the annulus is removed to create access to the disc space. The disc space can then be prepared for fusion. A hole can then be created in the endplate 72. The device 100 (e.g., a wicking material and/or perforated tube) can be placed in the hole. The interbody device can then be placed within the disc space. In another embodiment, a portion of the annulus is removed to create access to the disc space. The disc space is prepared for fusion. The interbody device is then positioned in the disc space. A hole can then be created in the endplate. The device 100 can then be placed within the hole. In another embodiment, a portion of the annulus is removed to create access to the disc space. The disc space is then prepared for fusion. A hole is then created in the endplate. The interbody device can then be placed in the disc space and then the device 100 can then be placed within the hole.

Accordingly, there are various options for creating the hole in the endplate for placement of the device 100. For example, the hole can be formed before or after the placement of the interbody device. In addition, as described above, the hole can be created using, for example, a drilling jig that attaches to, for example, the disc space, interbody implant, or the anterior surface of the vertebral body. The interbody implant 200 may have an access channel 210 on its trailing surface configured to accommodate the device 100, to permit insertion of the device 100 after implantation of the interbody spacer 200. In some embodiments, the interbody implant may further comprise a plug or other barrier which may be placed in or against the access channel, such that the nutrients wicked into one or more central cavities of the interbody spacer may be generally contained there. In such embodiments, the second end of the interbody device may be configured such that it may be implanted through the access channel, but, upon insertion, comes to rest in a central cavity in the interbody spacer 200 between the two vertebral endplates 72 (superior and inferior). In some embodiments, more than one access channel 210 may be provided and more than one wicking device may be implanted.

Although these devices and methods have been disclosed in the context of certain preferred embodiments and examples, it will be understood by those skilled in the art that the present application extend beyond the specifically disclosed embodiments to other alternative embodiments and/or uses of the devices and obvious modifications and equivalents thereof. In addition, while several variations of the devices have been shown and described in detail, other modifications, which are within the scope of this application, will be readily apparent to those of skill in the art based upon this disclosure. It is also contemplated that various combination or sub-combinations of the specific features and aspects of the embodiments may be made and still fall within the scope of the present disclosure. It should be understood that various features and aspects of the disclosed embodiments can be combined with or substituted for one another in order to form varying modes of the disclosed devices. Thus, it is intended that the scope of at least some of the devices herein disclosed should not be limited by the particular disclosed embodiments described above.

What is claimed is:

1. A method for promoting fusion within a spine segment having a disc comprising a top surface, a bottom surface, and an outer side surface extending between the top surface and the bottom surface, comprising:

accessing an endplate of a vertebral body;

perforating the endplate of the vertebral body;

providing an implant for treating the spine comprising a porous member configured to promote transfer of nutrients, wherein a first end of the implant has indentations, holes or pores optimized for wicking nutrients into the interior of the implant and the second end of the implant has different indentations, holes, or pores optimized for delivery of the nutrients to the surrounding area of the intervertebral space;

inserting the implant into a spinal column in a specific orientation such that the first end of the implant is adjacent a cancellous bone portion of the vertebral body and the second end of the implant extends into the disc, and wherein the porous member has a reduced configuration to allow implantation and an expanded configuration after implantation.

2. The method of claim 1, wherein accessing the endplate of the vertebral body comprises creating an opening at the outer side surface of the disc and creating a path starting at the opening and extending to the endplate.

3. The method of claim 2, wherein perforating the endplate of the vertebral body comprise perforating the endplate of the vertebral body after creating the path starting at the opening.

4. The method of claim 2, wherein inserting the implant into the spinal column comprises inserting the implant into the path so that the first end of the implant is adjacent the cancellous bone portion and the second end of the implant extends into the disc.

5. The method of claim 1, wherein the transfer of nutrients comprises the transfer of nutrients from the vertebral body to the disc.

6. The method of claim 1, wherein the porous member is made of a wicking material.

7. The method of claim 1, wherein the porous member is an absorbent material.

8. The method of claim 1, wherein the porous member is flexible.

9. The method of claim 1, wherein the endplate faces a downward direction.

10. A method for promoting fusion within a spine segment having a disc comprising a top surface, a bottom surface, and an outer side surface extending between the top surface and the bottom surface, comprising:

accessing an endplate of a vertebral body;

perforating the endplate of the vertebral body;

providing an implant for treating the spine comprising a porous member configured to promote transfer of nutrients;

inserting the implant into a spinal column so that a first end of the implant is adjacent a cancellous bone portion of the vertebral body and a second end of the implant extends into the disc, wherein the porous member has a first porous section optimized for wicking nutrients into the interior of the implant, and a second porous section optimized for delivery of the nutrients to the surrounding area, and wherein the porous member has a reduced configuration to allow implantation and an expanded configuration after implantation.

11. The method of claim 10, wherein accessing the endplate of the vertebral body comprises creating an opening at the outer side surface of the disc and creating a path starting at the opening and extending to the endplate.

12. The method of claim 11, wherein perforating the endplate of the vertebral body comprise perforating the endplate of the vertebral body after creating the path starting at the opening.

13. The method of claim 11, wherein inserting the implant into the spinal column comprises inserting the implant into the path so that the first end of the implant is adjacent the cancellous bone portion and the second end of the implant extends into the disc.

14. A method for promoting fusion within a spine segment having a disc comprising a top surface, a bottom surface, and an outer side surface extending between the top surface and the bottom surface, comprising:

accessing an endplate of a vertebral body;

perforating the endplate of the vertebral body;

providing an implant for treating the spine comprising a porous member configured to promote transfer of nutrients;

inserting the implant into a spinal column so that a first end of the implant is adjacent a cancellous bone portion of a vertebra and a second end of the implant extends into the disc, wherein the porous member has a reduced configuration to allow implantation and an expanded configuration after implantation.

15. The method of claim 14, wherein accessing the endplate of the vertebral body comprises creating an opening at the outer side surface of the disc and creating a path starting at the opening and extending to the endplate.

16. The method of claim 15, wherein perforating the endplate of the vertebral body comprise perforating the endplate of the vertebral body after creating the path starting at the opening.

17. The method of claim 15, wherein inserting the implant into the spinal column comprises inserting the implant into the path so that the first end of the implant is adjacent the cancellous bone portion and the second end of the implant extends into the disc.

18. The method of claim 14, wherein the implant has an end with a porous structure optimized for wicking nutrients into the interior of the implant and another end with a porous structure optimized for delivery of the nutrients to the surrounding area.

* * * * *